(12) United States Patent
Ryu et al.

(10) Patent No.: US 8,961,497 B2
(45) Date of Patent: Feb. 24, 2015

(54) PORTABLE VACUUM GENERATION DEVICE, AND MEDICAL SUCTION DEVICE USING SAME

(75) Inventors: Hyun Seung Ryu, Yongin-si (KR); Joon Pio Hong, Seongnam-si (KR); Myong Chul Park, Gunpo-si (KR); Jun Kyu Park, Seongnam-si (KR)

(73) Assignee: Bioalpha Inc. (KR)

( * ) Notice: Subject to any disclaimer, the term of this patent is extended or adjusted under 35 U.S.C. 154(b) by 0 days.

(21) Appl. No.: 13/513,312

(22) PCT Filed: Nov. 3, 2010

(86) PCT No.: PCT/KR2010/007701
§ 371 (c)(1),
(2), (4) Date: Jun. 1, 2012

(87) PCT Pub. No.: WO2011/068310
PCT Pub. Date: Jun. 9, 2011

(65) Prior Publication Data
US 2012/0259299 A1 Oct. 11, 2012

(30) Foreign Application Priority Data
Dec. 4, 2009 (KR) .......................... 10-2009-0119862

(51) Int. Cl.
*A61M 27/00* (2006.01)
*A61M 1/00* (2006.01)

(52) U.S. Cl.
CPC ........... *A61M 1/0031* (2013.01); *A61M 1/0088* (2013.01); *A61M 2205/8206* (2013.01)
USPC ............................ 604/543; 604/313; 604/319

(58) Field of Classification Search
CPC ............ A61M 1/0031; A61M 1/0088; A61M 1/0037; A61M 2205/8206; A61M 2205/18; A61M 2205/3344; A61M 2205/8212; A61M 27/00

USPC .......................................... 604/319, 313, 354
See application file for complete search history.

(56) References Cited

U.S. PATENT DOCUMENTS 6,719,080 B1 * 4/2004 Gray, Jr. ......................... 180/165
6,998,993 B2 * 2/2006 Wang et al. .................... 340/635

(Continued)

FOREIGN PATENT DOCUMENTS

JP      2002065843      3/2002
KR   1020040039301      5/2004

OTHER PUBLICATIONS

International Search Report—PCT/KR2010/007701 dated Jul. 20, 2011.

*Primary Examiner* — Philip R Wiest
*Assistant Examiner* — Ariana Zimbouski
(74) *Attorney, Agent, or Firm* — Cantor Colburn LLP

(57) ABSTRACT

Provided is a portable vacuum generator that can effectively save battery power of a vacuum pump for absorbing exudates from a suction head that is connected to a tube, and a medical suction device using the same. The medical suction device includes: a connection tube whose one end is connected to a connector of the suction head; and a vacuum generator including a vacuum pump that is connected to the other end of the connection tube and having a motor for generating negative pressure, and a vacuum pump controller that controls a power supply for the vacuum pump so as to maintain a vacuum state, in which the vacuum pump controller blocks the power supply for the vacuum pump until pressure of the vacuum pump falls down to preset minimum pressure in the case that the current pressure that is applied to the vacuum pump reaches preset maximum pressure, and drives the vacuum pump until pressure of the vacuum pump reaches the preset maximum pressure in the case that the current pressure falls down to the preset minimum pressure.

4 Claims, 5 Drawing Sheets

(56) References Cited

U.S. PATENT DOCUMENTS

| | | | |
|---|---|---|---|
| 7,553,306 B1* | 6/2009 | Hunt et al. | 604/543 |
| 2005/0057195 A1* | 3/2005 | Murlasits | 315/360 |
| 2006/0004492 A1* | 1/2006 | Terlson et al. | 700/276 |
| 2008/0232977 A1* | 9/2008 | Pan et al. | 417/44.11 |
| 2008/0281281 A1 | 11/2008 | Meyer et al. | |
| 2009/0043268 A1 | 2/2009 | Eddy et al. | |
| 2009/0204085 A1* | 8/2009 | Biggie et al. | 604/313 |
| 2009/0264837 A1* | 10/2009 | Adahan | 604/290 |

* cited by examiner

PORTABLE VACUUM GENERATION DEVICE, AND MEDICAL SUCTION DEVICE USING SAME

TECHNICAL FIELD

The present invention relates to a portable vacuum generator that is used for treatment of wounds, and a medical suction device using the same, and more particularly to a portable vacuum generator that can effectively save battery power of a vacuum pump for absorbing exudates from a suction head that is connected to a tube, and a medical suction device using the same.

BACKGROUND ART

In the department of surgery, therapy using negative pressure is being performed for the purpose of promoting healing of surgical wound portions. In order to heal wound portions by using negative pressure, a suction head is associated with a vacuum device, that is, a suction device and is used for healing the wound portions. During healing the wound portions, the suction head is connected to the suction device to maintain proper negative pressure.

Typically, suction lines that are connected to vacuum pumps are built in wails of hospital wards or operating rooms in a hospital. A medical suction device is provided to control suction pressure or process inhaled objects by opening or closing valves provided in the suction lines.

First, a porous pad is attached to a wound portion and then surgical drapes are attached to cover the porous pad and the wound portion together, to thus seal the wound portion. One end of a drain tube is directly inserted into the porous pad at a state where the wound portion has been sealed, and a suction device that is connected to the other end of the drain tube is driven, to thus generate negative pressure in the inner side of the drapes. By doing so, exudates discharged from the wound is absorbed into the porous pad and discharged through the drain tube, to accordingly heal the wound.

In this case, the porous pad helps exudates escaping through the drain tube smoothly, by maintaining a predetermined gap between surface of a wound and drapes to thus continuously maintain negative pressure in the inside of the drapes.

Wall-mounted suction devices that are provided in the medical facilities of hospitals or portable suction devices with built-in electric pumps are used as the suction devices. Drain tubes are generally connected to the wall-mounted suction devices, respectively.

A conventional portable suction device will be described with reference to FIG. 1.

A portable suction device shown in FIG. 1 is disclosed in Korean Patent-Publication No. 10-0842895 entitled a tissue treatment apparatus using vacuum. The conventional suction device 10 includes: a porous pad 11; an electric pump 14 for giving negative pressure to a wound portion; an air-tight dressing 13; a connector 17 that hydraulically connects one end of a connection tube 16 with the dressing 13; a container 18 that is separably connected to the other end of the connection tube 16; a primary filter 20 that is positioned between the container 18 and the electric pump 14; a secondary filter 22 that is positioned between the primary filter 20 and the electric pump 14; and a pump drive control system 80 that changes pressure according to an interval of time to thus control the pressure applied to the electric pump 14.

The pump drive control system 80 determines an optimal driving frequency of the electric pump 14 that receives the pressure that is measured and transferred by a pressure sensor 82. The optimum driving frequency of the electric pump 14 is continuously determined by the pump drive control system 80. The electric pump 14 is driven at the determined optimum driving frequency.

However, the pump drive control system 80 changes the optimal driving frequency at which the electric pump 14 is driven, and contributes to extend battery life in a manner that pressure is controlled downwards when the pressure rises up to the maximum pressure, and is controlled upwards when the pressure falls down to the minimum pressure. However, since a pump drive power supply for driving a pump is not controlled on a turn-on and turn-off mode basis, it is limited to save the pump drive power supply using battery power.

In addition, since the pressure of the electric pump 14 can be maximized by using the pump drive control system 80 employing a variety of frequencies, the conventional suction device maximizes flow of the electric pump 14, that is, difference in negative pressure, to accordingly fail to minimize operation of the pump and restrict reduction of noise that occurs from the pump.

in FIG. 1, a reference numeral 12 denotes a wound portion, a reference numeral 15 denotes a secondary malodorous vapor filter, a reference numeral 23 denotes a malodorous vapor filter, a reference numeral 24 denotes a re-sealable access filter, a reference numeral 25 denotes an external exhaust filter, a reference numeral 84 denotes a controller, and a reference numeral 86 denotes a driving circuit.

DISCLOSURE

Technical Problem

To solve the above problems or defects, it is an object of the present invention to provide a portable vacuum generator that control a pump drive power supply to thus extend a battery life, in which the pump drive power supply is controlled in a manner that the pump drive power supply is blocked until pressure of a pump falls down to preset minimum pressure in the case that the pressure that is provided by the pump reaches preset maximum pressure so that exudates of a wound portion is discharged through a drain tube at a vacuum mode, and a medical suction device using the same.

Technical Solution

To accomplish the above and other objects of the present invention, according to an aspect of the present invention, there is provided a medical suction device for discharging exudates of a wound portion on a negative pressure basis, the medical suction device comprising:

a porous pad attached to the wound portion;

a suction head that is positioned on top of the porous pad and thus collects and guides the exudates absorbed by the porous pad;

drapes that seal the wound portion except for a connector of the suction head;

a connection tube whose one end is connected to the connector of the suction head; and a vacuum generator including a vacuum pump that is connected to the other end of the connection tube and having a motor for generating negative pressure, and a vacuum pump controller that controls a power supply for the vacuum pump so as to maintain a vacuum state, wherein the vacuum pump controller blocks the power supply for the vacuum pump until pressure of the vacuum pump falls down to preset minimum pressure in the case that the current pressure that is applied to the vacuum pump reaches preset maximum pressure, and drives the vacuum pump until pressure of the vacuum pump reaches the preset maximum pressure in the case that the current pressure falls down to the preset minimum pressure.

Preferably but not necessarily, the vacuum pump controller comprises:

a pressure sensor for sensing pressure applied to the vacuum pump;

a controller that generates a first control signal for blocking a power supply for a pump driving motor until the pressure of the pump falls down to the preset minimum pressure in the case that the current pressure reaches the preset maximum pressure in response to the current pressure that is detected by the pressure sensor and applied to the vacuum pump, and that generates a second control signal for driving the pump driving motor until the current pressure reaches the preset maximum pressure in the case that the current pressure falls down to the preset minimum pressure;

a first relay that is connected to an output end of the controller and is activated in response to the first control signal of the controller and is deactivated in response to the second control signal; and a second relay that is linked to the first relay and operates in a complimentary form, and that is deactivated when the first relay is activated to thus block the power supply for the pump driving motor, and is activated when the first relay is deactivated to thus resume the power supply for the pump driving motor.

Preferably but not necessarily, the controller further comprises: an input unit for setting the maximum pressure and the minimum pressure for the vacuum pump.

Preferably but not necessarily, the medical suction device further comprises: a sewage chamber that is detachably disposed between the vacuum pump and the connection tube of the vacuum generator, in which the exudates discharged according to the negative pressure is stored.

Preferably but not necessarily, the power supply for the vacuum generator is a battery or a commercialized power supply.

According to another aspect of the present invention, there is also provided a portable vacuum generator comprising:

a vacuum pump having a motor for generating negative pressure according to driving of the motor;

a pressure sensor for sensing pressure applied to the vacuum pump;

a controller that generates a first control signal for blocking a power supply for a pump driving motor until, pressure of the pump falls down to the preset minimum pressure in the case that the current pressure reaches the preset maximum pressure in response to the current pressure that is detected by the pressure sensor and applied to the vacuum pump, and that generates a second control signal for driving the pump driving motor until the current pressure reaches the preset maximum pressure in the case that the current pressure falls down to the preset minimum pressure;

a first relay that is connected to an output end of the controller and is activated in response to the first control signal of the controller and is deactivated in response to the second control signal; and a second relay that is linked to the first relay and operates in a complimentary form, and that is deactivated when the first relay is activated to thus block the power supply for the pump driving motor, and is activated when the first relay is deactivated to thus resume the power supply for the pump driving motor.

Preferably but not necessarily, the power supply for the vacuum pump is a battery or a commercialized power supply.

Advantageous Effects

Thus, a portable vacuum generator according to the present invention controls a pump drive power supply to thus extend a battery life, in which the pump drive power supply is controlled in a manner that the pump drive power supply is blocked until pressure of a pump falls down to preset minimum pressure in the case that the pressure that is provided by the pump reaches preset maximum pressure so that exudates of a wound portion is discharged through a drain tube at a vacuum mode.

In addition, the present invention controls a power supply to be turned on/off to thus minimize operation of the pump and thereby minimize noise of the pump.

BEST MODE

Hereinafter, a preferred embodiment of the present invention will be described in detail with reference to the accompanying FIGS. 2 to 7.

Figure 1:
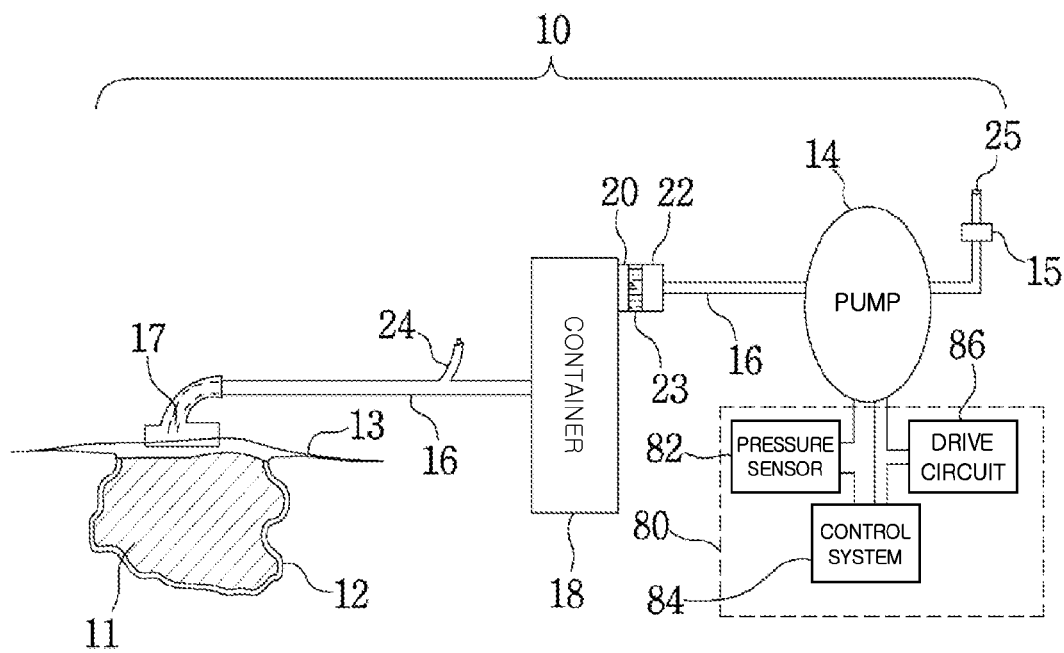
FIG. 1 is a schematic diagram for explaining a conventional suction device.
Figure 2:
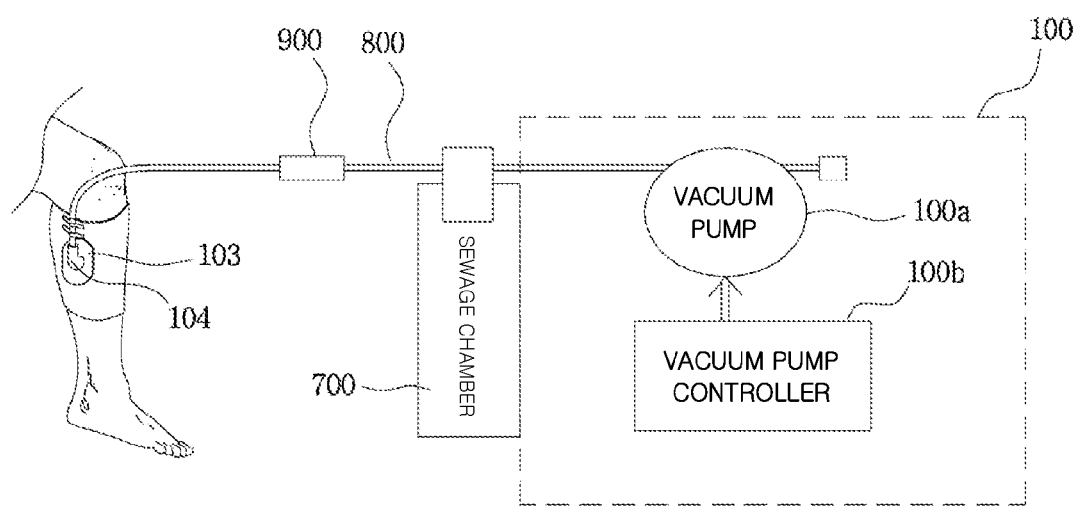
FIGS. 2 and 3 are schematic diagrams showing a medical suction device according to an embodiment of the present invention.
Figure 3:
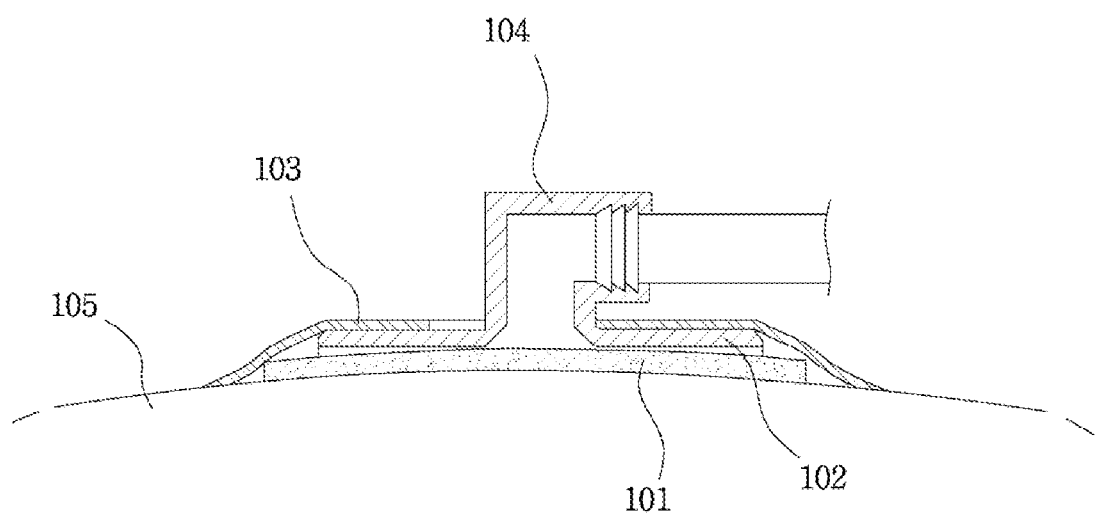
Figure 4:
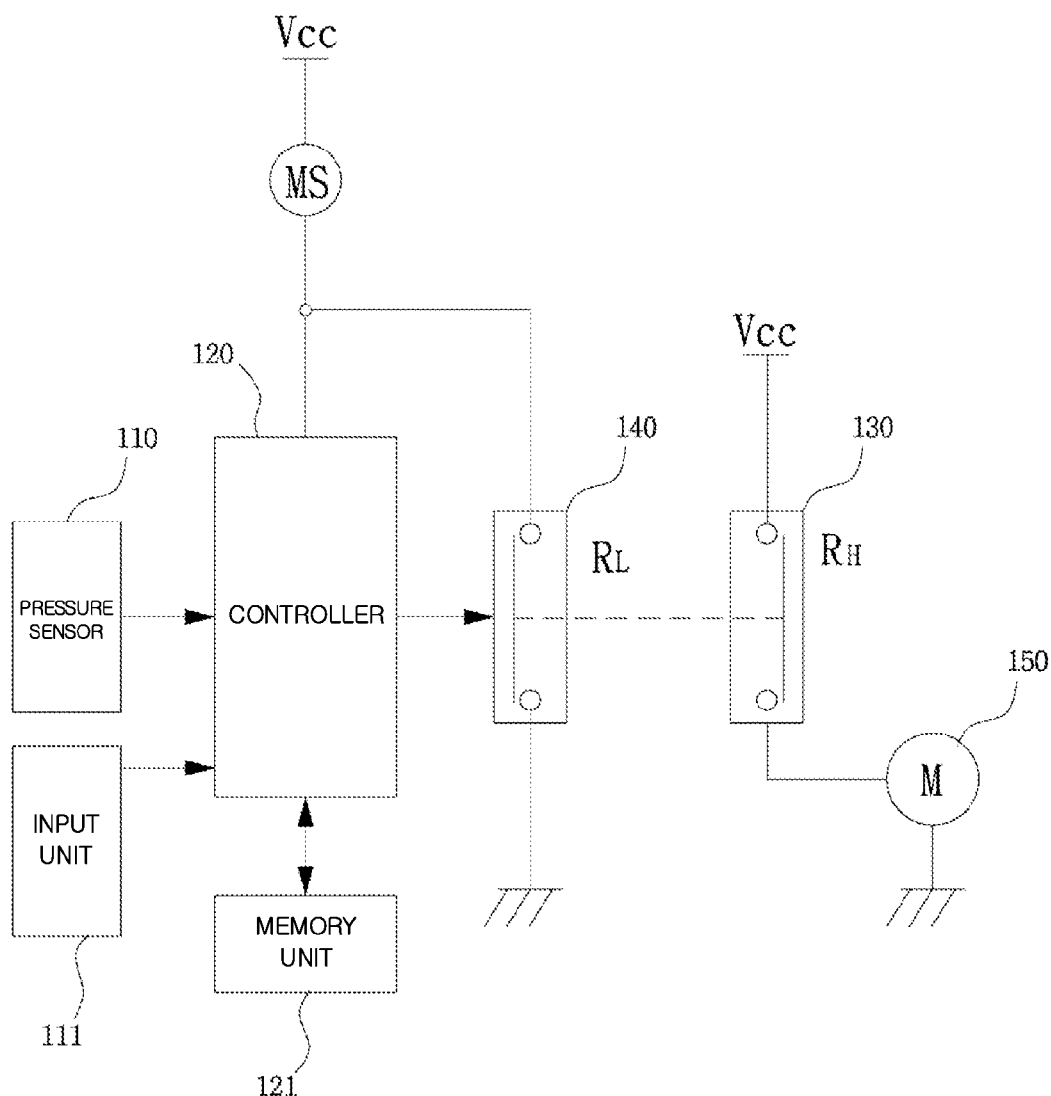
FIG. 4 is a detailed block diagram showing a vacuum pump controller of FIG. 2.
Figure 5:
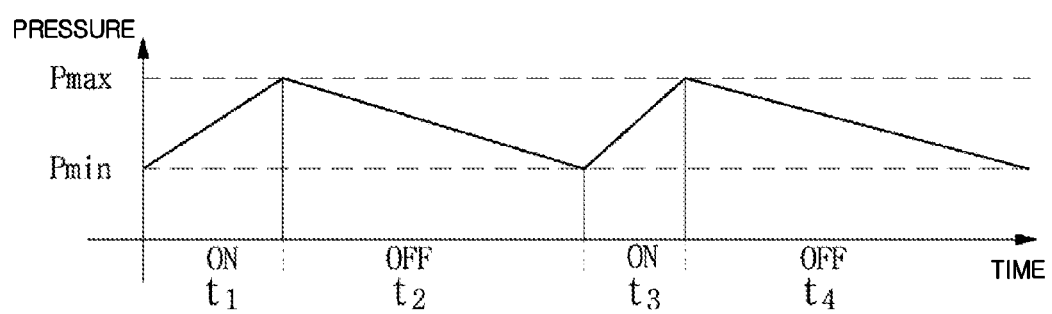
FIG. 5 is a graphical view showing relationship between pressure and time for controlling the vacuum pump.
Figure 6:
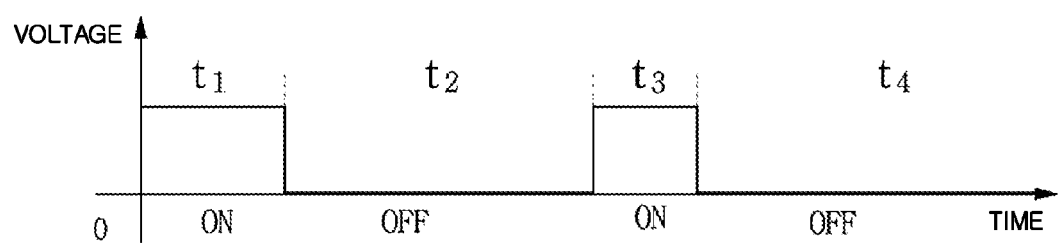
FIG. 6 is a timing diagram showing relationship between voltage and time for controlling the vacuum pump.
Figure 7:
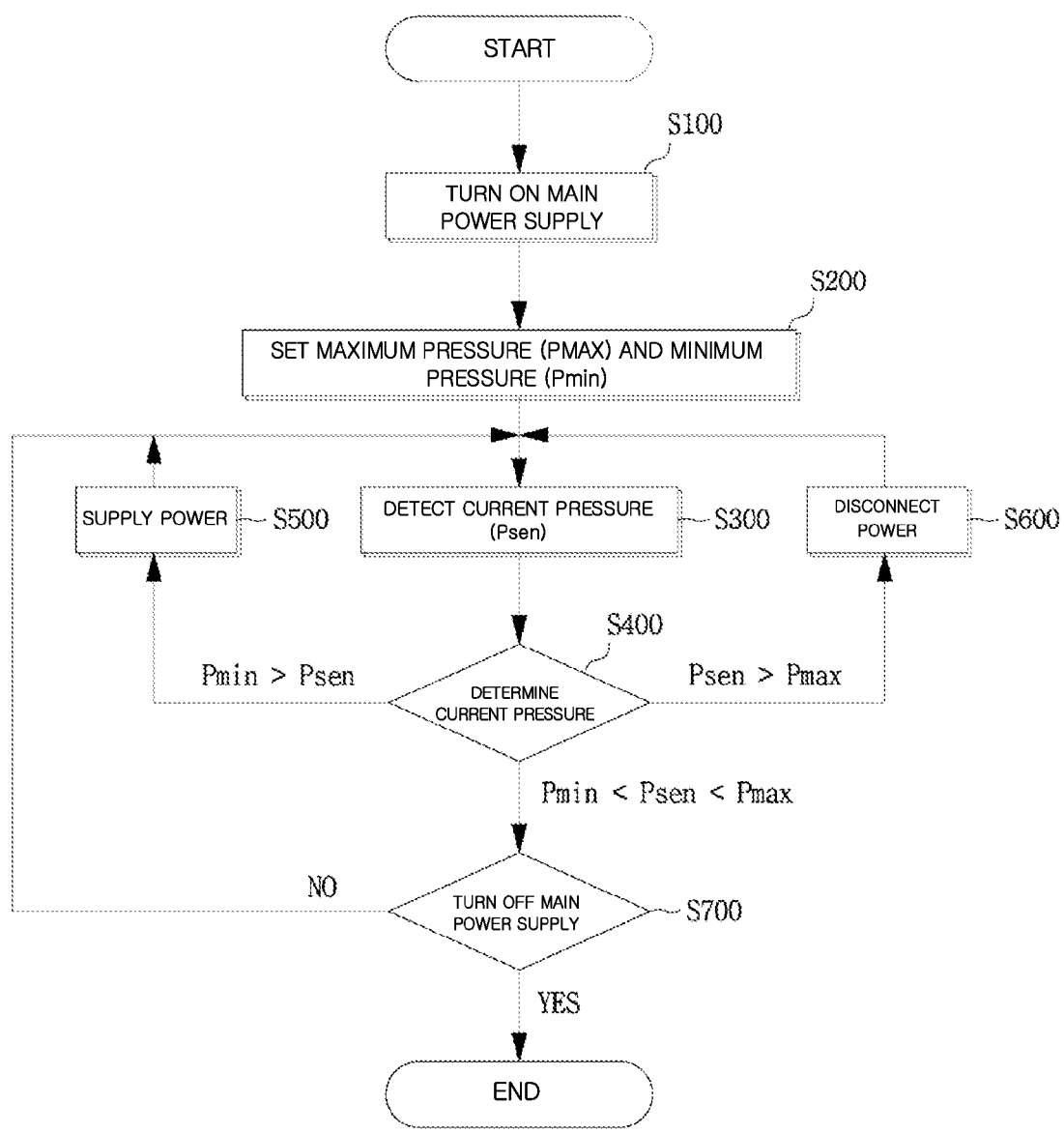
FIG. 7 is a flowchart view for explaining a control operation of a vacuum pump according to the present invention.

FIG. 2 is a schematic diagram showing a suction device according to an embodiment of the present invention, and FIG. 3 is a cross-sectional view of a suction head. FIG. 4 is a detailed block diagram showing a vacuum pump controller of FIG. 2. FIG. 5 is a graphical view showing relationship between pressure and time for controlling the vacuum pump. FIG. 6 is a timing diagram showing relationship between voltage and time for controlling the vacuum pump. FIG. 7 is a flowchart view for explaining a control operation of a vacuum pump according to the present invention.

Refer to FIG. 2, the medical suction device according to the present invention includes: a portable vacuum generator 100 that provides a vacuum source; a sewage chamber 700 that stores exudates discharged from a wound portion according to negative pressure supplied from the vacuum generator 100; a connection tube 800 that is connected to the sewage chamber 700 so that the exudates are guided to the sewage chamber 700; and a connector 900 that connects the vacuum generator 100 with drapes 103 at one side of the connection tube 800, to thus transfer the negative pressure to the drapes 103.

A power supply for the medical suction device according to the present invention, particularly for the portable vacuum generator, basically includes a battery power supply that can be used during moving. In addition, it is desirable that the vacuum generator further includes a power supply having a built-in AC/DC converter, that is, an adaptor (not shown) that saves power of the battery at a standstill state, and that is able to use a commercial power supply that is externally supplied.

Referring to FIG. 3, a porous pad 101 is attached to a wound portion 105, and a suction head 102 is placed on top of the porous pad 101, to thus collect and guide exudates absorbed by the porous pad 101. The surgical drapes 103 for sealing the wound portion 105 are attached on the suction head 102 and the wound portion 105 except for a connector 104 of the suction head 102.

The other end of the connection tube 800 is connected to the connector 104 of the suction head 102, and the suction head 102 discharges the exudates absorbed by the porous pad 101 attached to the wound portion 105 sealed by the surgical drapes 103, by using the negative pressure.

Meanwhile, the vacuum generator 100 includes a vacuum pump 100a and a vacuum pump controller 100b for controlling the vacuum pump 100a. The vacuum pump 100a provides the negative pressure for discharging the exudates from the inside of the drapes through the connection tube 800. The vacuum pump controller 100b controls the vacuum pump 100a so as to minimize consumption of the battery while maintaining the preset, negative pressure.

As shown in FIG. 4, the vacuum pump controller 100b includes:

a pressure sensor 110 or sensing pressure applied to the vacuum pump 100a;

a controller 120 that receives the pressure of the pressure sensor 110 and controls a motor 150 for driving the vacuum pump 100a;

the motor 150 that is built in the vacuum pump 100a and provides a rotating force for generating negative pressure; and first and second relays 140 and 130 that control power supply with respect to the motor 150 under the control of the controller 120.

The first relay ($R_L$) 140 is connected to the controller 120 and is turned on or turned off by the controller 120, to thus turn on or turn off the second relay ($R_H$) 130.

In addition, the second relay ($R_H$) 130 operates in conjunction with the first relay 140 that operates under the control of the controller 120, and is set in opposition to the state of the first relay 140, to thus feed or block power Vcc for driving the motor 150.

An operation of the vacuum generator 100 having the above-described configuration will be described with reference to FIGS. 5, 6 and 7.

When a user turns on a main power switch MS of the vacuum generator 100 in order to discharge the exudates from the drapes 103, main power is supplied to the vacuum generator 100 (S100). The user presets maximum pressure and minimum pressure for controlling the vacuum pump 100a in a memory unit 121 that is connected to or built in the controller 120 through an input device 111, at a state where the main power has been supplied (S200).

Referring to FIG. 5, the maximum pressure set and stored in the memory unit 121 of the controller 120 is indicated as Pmax, and the minimum pressure thereof is indicated as Pmin.

When the vacuum generator 100 starts to drive, the controller 120 detects current pressure Psen of the vacuum pump 100a that is input from the pressure sensor 110 (S300). When the controller 120 judges that the detected current pressure Psen is lower than the preset minimum pressure Pmin (S400), it controls the first relay 140 to be turned off (deactivated), and accordingly controls the second relay 130 to be turned on (activated) so that power Vcc is supplied for the motor 150 (S500).

Then, the vacuum pump 100a generates negative pressure according to driving of the motor 150. Thus, if the exudates are absorbed from the drapes 103, the absorbed exudates are collected in the sewage chamber 700 through connection tube 800, and the pressure sensor 110 senses the pressure of the vacuum pump 100a continuously to then be output to the controller 120.

This case corresponds to an interval of t1 in FIG. 5, in which the current pressure Psen becomes continuously higher than the minimum pressure Pmin, and the power Vcc for the motor 150 is turned on as shown in FIG. 6.

Since then, the controller 120 continuously detects the current pressure Psen. Thus, if the controller 120 judges that the current pressure Psen is higher than the maximum pressure Pmax (S400), the first relay 140 is turned on, and accordingly the second relay 130 is turned off, to thereby block the power Vcc for the motor 150 (S600).

When the power supply for the motor is blocked, leakage occurs at the junction of the drapes 103, the connection tube 800, and the connector 900. As a result, the pressure of the vacuum pump 100a will drop slowly.

This case corresponds to an interval of t2 in FIG. 5, in which the current pressure Psen is consistently lowered in comparison with the maximum pressure Pmax, and the power Vcc for the motor 150 is turned off as shown in FIG. 6.

Since then, the controller 120 continuously detects the current pressure Psen. Thus, if the current pressure Psen is lower than the minimum pressure Pmin, the power Vcc is supplied again for the motor 150. Thus, the power is supplied for the motor 150 as shown in an interval of t3 in FIG. 5. Then, if the current pressure Psen gets higher than the minimum pressure Pmin, the power is again blocked for the motor 150 as shown in an interval of t4 in FIG. 5.

In other words, the controller 120 controls driving of the first and second relays 140 and 130 to disconnect the power supply for the motor 150 if the current pressure Psen rises up to the preset maximum pressure Pmax or above, and to supply the power for the motor 150 if the current pressure Psen falls down to the preset minimum pressure Pmin or below.

In the present invention, after the initial main power is applied, it is desirable that driving of the pump at the initial state, that is, a running time t1 of the motor 150 reaches the maximum negative pressure within ten (10) seconds, and the negative pressure lasts for at least seven minutes or more at intervals of t2 and t4. In addition, it is desirable that restarting reaches the proper negative pressure within three (3) seconds in a driving interval of t3 for the pump motor 150.

Finally, if the user does not turn off the main power switch MS, the above-described turn-on/turn-off control is performed repeatedly.

EXAMPLE 1

Comparison Tests For Battery Life at Operating Modes

In the present invention, the following experiment was carried out in order to verify operation of a vacuum generator.

A porous polyurethane foam pad of 160×125×30 mm having an average particle diameter in size of 450 microns was attached on a wound portion of a mannequin model with the wound portion, and a suction head was mounted on the porous polyurethane foam pad. Then, the suction head and the porous polyurethane foam pad were completely sealed with drapes. The suction head was connected to a connection tube connected with a vacuum pump of the vacuum generator. Then, a battery power supply for the vacuum generator was activated after a battery power supply was completely charged. Then, time taken until the battery power supply was completely discharged and thus the vacuum generator stopped was measured.

Programmed vacuum generators were used as the vacuum generators, that is, the suction devices of Comparative Example 1, Comparative Example 2, and Example 1 (negative pressure range operating modes) according to the present invention, in which the same models of the vacuum generators were used but the different operating modes of the vacuum generators were used.

TABLE 1

| Item | Comparative Example 1 | Comparative Example 2 | Example 1 |
|---|---|---|---|
| Operating modes | continuous | intermittent | negative pressure range operating mode |
| Actual operating time | continuous operation | 5-minute operation, 2-minute stop | 3-minute stop, 3-second operation |
| Set negative pressure | 130 mmHg | 130 mmHg | stop at maximum 130 mmHg, operation at minimum 100 mmHg |
| Operating time | 183 minutes | 227 minutes | 10,918 minutes |

It can be seen that the battery operating time of the Example 1 greatly increases by sixty times in comparison with the Comparative Example 1 and by forty-eight times in comparison with the Comparative Example 2.

As it can be seen obviously from the comparison test, the vacuum generator 100 according to the present invention is not necessary to receive power but do not consume unnecessary power until the preset maximum pressure falls down to the preset, minimum pressure when a wound portion is treated, to thereby greatly extend the battery life.

EXAMPLE 2

Animal Tests For Healing Wound at Negative Pressure Modes

Six wounds were made on the back of a pig (each wound in size 6×6 cm, removal of the whole layer of the skin immediately before the muscles are exposed), and then respectively different range of the negative pressure operating modes (Comparative Example 1, Comparative Example 2, Example 1, Example 2, and Example 3) were applied to then be observed for nine days. The kinds of the negative pressure ranges that were applied for the wounds are shown in Table 2.

TABLE 2

The kinds of negative pressures applied to the wounds

| Class | Negative pressure operating modes |
|---|---|
| Comparative Example 2 | intermittent (5-minute operation 130 mmHg, 2-minute stop) |
| Example 1 | negative pressure range operating mode 130-100 mmHg |
| Example 2 | negative pressure range operating mode 130-70 mmHg |
| Example 3 | negative pressure range operating mode 130-50 mmHg |
| Comparative Example 1 | continuous (130 mmHg) |

As an evaluation in order to investigate regeneration of the tissue, blood flow and as proliferation of granulation tissue were observed.

As an experimental result, the blood flow measured at each wound portion by the Comparative Examples 1 and 2 and Examples 1 to 3 are shown in Table 3, in which the blood flow was expressed as a blood flow unit by perfusion unit. As the blood flow becomes large, cells are sufficiently supplied with nutrients to regenerate tissue, which will help the wound heal faster.

TABLE 3

Average blood flow measured in each wound portion

| Negative pressure | Average perfusion unit |
|---|---|
| Comparative Example 2 | 149 |
| Example 1 | 176 |
| Example 2 | 187 |
| Example 3 | 195 |
| Comparative Example 1 | 165 |

Proliferation of granulation tissue by negative pressure in the damaged tissue is shown in Table 4, in which height of the regenerated granulation tissue was measured for each period.

TABLE 4

Thickness of granulation tissue regenerated at negative pressure modes

| Period | Comparative Example 2 | Example 1 | Example 2 | Example 3 | Comparative Example 1 |
|---|---|---|---|---|---|
| Thickness of regenerated granulation tissue after nine days (mm) | 3.26 | 3.69 | 3.83 | 3.90 | 3.55 |

In the result of having observed blood flow and proliferation of granulation tissue in order to investigate a range of negative pressure that works effectively to regeneration of damaged tissues, the negative pressure range operating modes according to the present invention has a more blood flow and has a more quickly regenerated granulation tissue to thus confirm a more excellent tissue regeneration effect, in comparison with an existing continuous mode and an existing Intermittent negative pressure mode. Thus, a battery run-time can dramatically increase and a wound recovery rate also even more increases, to thereby provide a negative pressure mode that maximizes an effect for healing the wound and power-saving.

As a result, the user is not tied to a fixed drive source to thereby improve mobility of patients. This vacuum generator can be preferably applied for a portable electric vacuum pump.

As described above, the present invention has been described with respect to particularly preferred embodiments. However, the present invention is not limited to the above embodiments, and it is possible for one who has an ordinary skill in the art to make various modifications and variations, without departing off the spirit of the present invention. Thus, the protective scope of the present invention is not defined within the detailed description thereof but is defined by the claims to be described later and the technical spirit of the present invention.

Industrial Applicability

As described above, the present invention can be applied for a medical wound healing suction device that can be connected to a wound treatment material and can discharge exudates smoothly.

The invention claimed is:

1. A portable medical suction device for discharging exudates of a wound portion on a negative pressure basis, the medical suction device comprising:
   a porous pad capable of being attached to the wound portion;
   a suction head that is positioned on top of the porous pad and thus collects and guides the exudates absorbed by the porous pad;
   drapes that seal the wound portion except for a connector of the suction head;
   a connection tube whose one end is connected to the connector of the suction head;
   a vacuum generator including a vacuum pump that is connected to the other end of the connection tube and having a motor for generating negative pressure;
   a main power switch that turns on the vacuum generator;
   a battery that supplies power to the vacuum pump and allows the medical suction device to be portable; and
   a vacuum pump controller that controls the power supply from the battery and extends a life of the battery while maintaining pressure applied to the vacuum pump within a range of pressure between a preset minimum pressure of 50 millimeter of mercury (mmHg) and a preset maximum pressure of 130 mmHg,
   wherein the vacuum pump controller causes the exudates of the wound portion to be continuously discharged through a drain tube while the main power switch is on by repeating:
      blocking the power supply for the vacuum pump until pressure of the vacuum pump falls down to the preset minimum pressure in a case that a current pressure that is applied to the vacuum pump reaches the preset maximum pressure; and
      driving the vacuum pump until pressure of the vacuum pump reaches the preset maximum pressure in a case that the current pressure falls down to the preset minimum pressure,
   wherein the vacuum pump controller comprises:
      a pressure sensor for sensing pressure applied to the vacuum pump;
      a controller that generates a first control signal for blocking a power supply for a pump driving motor until the pressure of the pump falls down to the preset minimum pressure in the case that the current pressure reaches the preset maximum pressure in response to the current pressure that is detected by the pressure sensor and applied to the vacuum pump, and that generates a second control signal for driving the pump driving motor until the current pressure reaches the preset maximum pressure in the case that the current pressure falls down to the preset minimum pressure;
      a first relay that is connected to an output end of the controller and is activated in response to the first control signal of the controller and is deactivated in response to the second control signal; and
      a second relay that is linked to the first relay and operates in a complementary form, and that is deactivated when the first relay is activated to thus block the power supply for the pump driving motor, and is activated when the first relay is deactivated to thus resume the power supply for the pump driving motor.

2. The medical suction device according to claim 1, wherein the controller further comprises: an input unit for setting the maximum pressure and the minimum pressure for the vacuum pump.

3. The medical suction device according to claim 1, further comprising:
   a sewage chamber that is detachably disposed between the vacuum pump and the connection tube of the vacuum generator, in which the exudates discharged according to the negative pressure is stored.

4. A portable vacuum generator comprising:
   a main power switch for turning the portable vacuum generator on or off;
   a vacuum pump having a motor for generating negative pressure according to driving of the motor;
   a pressure sensor for sensing pressure applied to the vacuum pump;
   a battery that supplies power to the vacuum pump;
   a controller that extends life of battery while maintaining pressure of the vacuum pump within a range of pressure between a preset minimum pressure of 50 millimeter of mercury (mmHg) and a preset maximum pressure of 130 mmHg by repeated generating a first control signal for blocking the power supply for a pump driving motor until pressure of the pump falls down to preset minimum pressure in a case that a current pressure reaches preset maximum pressure in response to the current pressure that is detected by the pressure sensor and applied to the vacuum pump and a second control signal for driving the pump driving motor until the current pressure reaches the preset maximum pressure in a case that the current pressure falls down to the preset minimum pressure so that the exudates of the wound portion are continuously discharged through a drain tube at a vacuum mode while the main power switch is on;
   a first relay that is connected to an output end of the controller and is activated in response to the first control signal of the controller and is deactivated in response to the second control signal; and
   a second relay that is linked to the first relay and operates in a complementary form, and that is deactivated when the first relay is activated to thus block the power supply for the pump driving motor, and is activated when the first relay is deactivated to thus resume the power supply for the pump driving motor.

* * * * *